(12) United States Patent
Levine et al.

(10) Patent No.: US 12,690,858 B2
(45) Date of Patent: Jul. 28, 2026

(54) SYSTEMS AND METHODS FOR ESTIMATING NEEDLE POSE

(71) Applicant: Covidien LP, Mansfield, MA (US)

(72) Inventors: Steven J. Levine, Framingham, MA (US); Meir Rosenberg, Newton, MA (US)

(73) Assignee: Covidien LP, Mansfield, MA (US)

( * ) Notice: Subject to any disclaimer, the term of this patent is extended or adjusted under 35 U.S.C. 154(b) by 210 days.

(21) Appl. No.: 18/283,118

(22) PCT Filed: Apr. 13, 2022

(86) PCT No.: PCT/IB2022/053479
§ 371 (c)(1),
(2) Date: Sep. 20, 2023

(87) PCT Pub. No.: WO2022/219559
PCT Pub. Date: Oct. 20, 2022

(65) Prior Publication Data

US 2024/0164765 A1     May 23, 2024

Related U.S. Application Data

(60) Provisional application No. 63/175,067, filed on Apr. 15, 2021.

(51) Int. Cl.
A61B 17/46       (2006.01)
A61B 17/04       (2006.01)
(Continued)

(52) U.S. Cl.
CPC .......... A61B 17/0469 (2013.01); A61B 34/10 (2016.02); A61B 34/20 (2016.02);
(Continued)

(58) Field of Classification Search
CPC ..... A61B 17/0469; A61B 34/10; A61B 34/20; A61B 34/32; A61B 90/361;
(Continued)

(56) References Cited

U.S. PATENT DOCUMENTS

| | | | |
|---|---|---|---|
| 2014/0323854 A1* | 10/2014 | Takeda | A61B 8/5215 |
| | | | 600/424 |
| 2018/0185113 A1* | 7/2018 | Gregerson | G06T 7/74 |

(Continued)

FOREIGN PATENT DOCUMENTS

| | | | | |
|---|---|---|---|---|
| EP | 3666160 A1 | 6/2020 | | |
| WO | WO-2021146339 A1 * | 7/2021 | | A61B 34/32 |
| WO | 2021158328 A1 | 8/2021 | | |

OTHER PUBLICATIONS

International Search Report and Written Opinion of the International Searching Authority issued in corresponding application PCT/IB2022/053479 mailed Jul. 22, 2022 (14 pages).

*Primary Examiner* — Neil R Mclean

(74) *Attorney, Agent, or Firm* — Carter, DeLuca & Farrell, LLP

(57) ABSTRACT

A system for tissue suturing guidance in a surgical site includes an imaging device configured to capture an image of a surgical needle within the surgical site and an imaging device control unit configured to control the imaging device. The imaging device control unit includes a processor and a memory. The memory stores instructions which, when executed by the processor, cause the system to capture an image of a surgical needle and a surgical tool within the surgical site via the imaging device, estimate a pose of the surgical needle based on the captured image, generate an augmented image based on the estimated pose of the surgical needle, and display on a display, the augmented image of the surgical needle.

20 Claims, 9 Drawing Sheets

(51) Int. Cl.

| | |
|---|---|
| *A61B 34/10* | (2016.01) |
| *A61B 34/20* | (2016.01) |
| *A61B 34/32* | (2016.01) |
| *A61B 90/00* | (2016.01) |
| *G06N 20/00* | (2019.01) |

(52) U.S. Cl.

CPC ............ *A61B 34/32* (2016.02); *A61B 90/361* (2016.02); *G06N 20/00* (2019.01); *A61B 2034/107* (2016.02); *A61B 2034/2065* (2016.02); *A61B 2090/365* (2016.02)

(58) Field of Classification Search

CPC ...... A61B 2034/107; A61B 2034/2065; A61B 2090/365; A61B 34/37; A61B 90/36; A61B 2090/306; A61B 2090/371; A61B 2090/3937; G06N 20/00; G06V 10/25; G06V 20/52; G06V 2201/034

USPC ........................................................ 382/128

See application file for complete search history.

(56) References Cited

U.S. PATENT DOCUMENTS

| | | | | |
|---|---|---|---|---|
| 2019/0125459 A1* | 5/2019 | Shelton, IV | ........... | G16H 40/63 |
| 2021/0307840 A1* | 10/2021 | Wolf | ................... | G06N 3/0464 |

* cited by examiner

10

Motion

10000

Start

10002 — Capture an image of a surgical needle within a surgical operative site

10004 — Estimate a pose of the surgical needle

10006 — Estimate a pose of the surgical tool

10008 — Generate a position refinement signal

10010 — Adjust the trajectory of the surgical needle based on the refinement signal 10012 — Estimate a pose or location of the tip of the surgical needle

SYSTEMS AND METHODS FOR ESTIMATING NEEDLE POSE

CROSS-REFERENCE TO RELATED APPLICATIONS

This application claims priority to PCT Application No. PCT/IB2022/053479 filed on Apr. 13, 2022, which claims the benefit of provisional U.S. patent application Ser. No. 63/175,067 filed on Apr. 15, 2021.

FIELD

The disclosure relates to robotics, and more specifically, to robotic surgical devices, assemblies, and/or systems for tissue suturing guidance in a surgical site.

BACKGROUND

Surgical suturing is an integral part of repairing tissue after a wound or surgical incision from minimally invasive surgery, among other things. Typically, suturing is a manual process where the clinician is left to their judgment and/or experience of the situation to determine various aspects of the suturing process to achieve proper suturing of the tissue.

Surgical suturing remains one of the most challenging tasks in robotic assisted surgery. Robotic surgical suturing includes a number of sub-tasks that are a cognitive challenge to a surgeon or clinician. These sub-tasks include (1) locating an appropriate needle penetration point; (2) grasping a needle perpendicularly to a pair of jaws; (3) envisioning of the needle trajectory; (4) approximating the abating tissue to the envisioned needle exit site; (5) inserting a tip of a needle (e.g., a curved needle) in the desired location; (6) rotating the needle in a trajectory that follows the needle curvature; (7) grasping the protruding needle or tip of the needle; (8) pulling the needle out in a path that follows the needle curvature; and (9) repeating or tying a suture attached to the needle.

Each of the above robotic surgical suturing sub-tasks is cognitively challenging, particularly in situations where the surgical tool kinematics are difficult to envision (curved or flexible tools) or in situations where the needle is not perpendicular to the pair of jaws of the tool or instrument.

Accordingly, there is an interest in reducing the cognitive load associated with sub-tasks 2-8 above and in supplementing the judgment or experience of clinicians and improving the efficacy of suturing outcomes.

SUMMARY

This disclosure relates to devices, systems, and methods for tissue suturing guidance in a surgical site. In accordance with aspects of the disclosure, a system for tissue suturing guidance in a surgical site includes an imaging device configured to capture an image of a surgical needle within the surgical site and an imaging device control unit configured to control the imaging device. The imaging device control unit includes a processor and a memory. The memory stores instructions which, when executed by the processor, cause the system to capture an image of a surgical needle and a surgical tool within a surgical site via the imaging device, estimate a pose of the surgical needle based on the captured image, generate an augmented image based on the estimated pose of the surgical needle, and display on a display, the augmented image of the surgical needle.

In an aspect of the disclosure, the instructions, when executed by the processor, may further cause the system to estimate a pose of the surgical tool based on the captured image, and generate a position refinement signal based on the estimated pose of the surgical needle and the estimated pose of the surgical tool.

In an aspect of the disclosure, the instructions, when executed by the processor, may further cause the system to receive a first control signal for the surgical tool, generate a second control signal based on the position refinement signal and the first control signal, and adjust a trajectory of the surgical needle based on the second control signal.

In an aspect of the disclosure, estimating the pose of the surgical needle may be based on a machine learning network.

In yet another aspect of the disclosure, the instructions, when executed by the processor, may cause the system to estimate a location of a tip of the surgical needle based on the captured image.

In a further aspect of the disclosure, the instructions, when executed by the processor, may further cause the system to generate a third control signal for adjusting a trajectory of the surgical needle based on the estimated pose of the tip of the surgical needle.

In yet a further aspect of the disclosure, the instructions, when executed by the processor, may further cause the system to determine whether the tip of the surgical needle is touching tissue and further augment the augmented image based on the surgical needle touching the tissue.

In an aspect of the disclosure, the instructions, when executed, may further cause the system to generate a third control signal for controlling a robotic surgical system based on the determined touch of the tissue by the tip of the surgical needle.

In a further aspect of the disclosure, the augmented image may include highlighting the surgical needle and/or highlighting the tip of the surgical needle.

In yet another aspect of the disclosure, the image may be a stereoscopic image.

In accordance with aspects of the disclosure, a computer-implemented method for tissue suturing guidance in a surgical site includes capturing an image of a surgical needle within the surgical site via an imaging device, estimating a location and/or direction of a tip of the surgical needle based on the captured image, estimating a pose of the surgical tool based on the captured image, and generating a position refinement signal based on the estimated location and/or direction of the tip of the surgical needle and the estimated pose of the surgical tool.

In a further aspect of the disclosure, the method may further include receiving a first control signal for the surgical tool, generating a second control signal based on the position refinement signal and the first control signal, and adjust a trajectory of the surgical needle based on the second control signal.

In yet a further aspect of the disclosure, the method may further include generating an augmented image based on the estimated location and/or direction of the tip of the surgical needle and displaying on a display, the augmented image of the surgical needle.

In yet another aspect of the disclosure, estimating the location and/or direction of the tip of the surgical needle may be based on a machine learning network.

In a further aspect of the disclosure, the method may further include estimating a location of a tip of the surgical needle based on the captured image.

In yet a further aspect of the disclosure, the method may further include generating a third control signal for adjusting a trajectory of the surgical needle based on the estimated pose of the tip of the surgical needle.

In yet another aspect of the disclosure, the method may further include determining whether the tip of the surgical needle is touching tissue and further augmenting the augmented image based on the surgical needle touching the tissue.

In a further aspect of the disclosure, the method may further include generating a third control signal for controlling a robotic surgical system based on the determined touch of the tissue by the tip of the surgical needle.

In an aspect of the disclosure, the augmented image may include highlighting the surgical needle and/or highlighting the tip of the surgical needle.

In accordance with the disclosure, a non-transitory storage medium that stores a program causing a computer to execute a computer-implemented method for tissue suturing guidance in a surgical site is presented. The computer-implemented method includes capturing an image of a surgical needle a surgical needle within the surgical site via an imaging device, estimating a pose of the surgical needle based on the captured image, estimating a pose of the surgical tool based on the captured image, and generating a position refinement signal based on the estimated pose of the surgical needle and the estimated pose of the surgical tool.

Further details and aspects of various embodiments of the disclosure are described in more detail below with reference to the appended figures.

BRIEF DESCRIPTION OF THE DRAWINGS

Embodiments of the disclosure are described herein with reference to the accompanying drawings, wherein.

Figure 1:
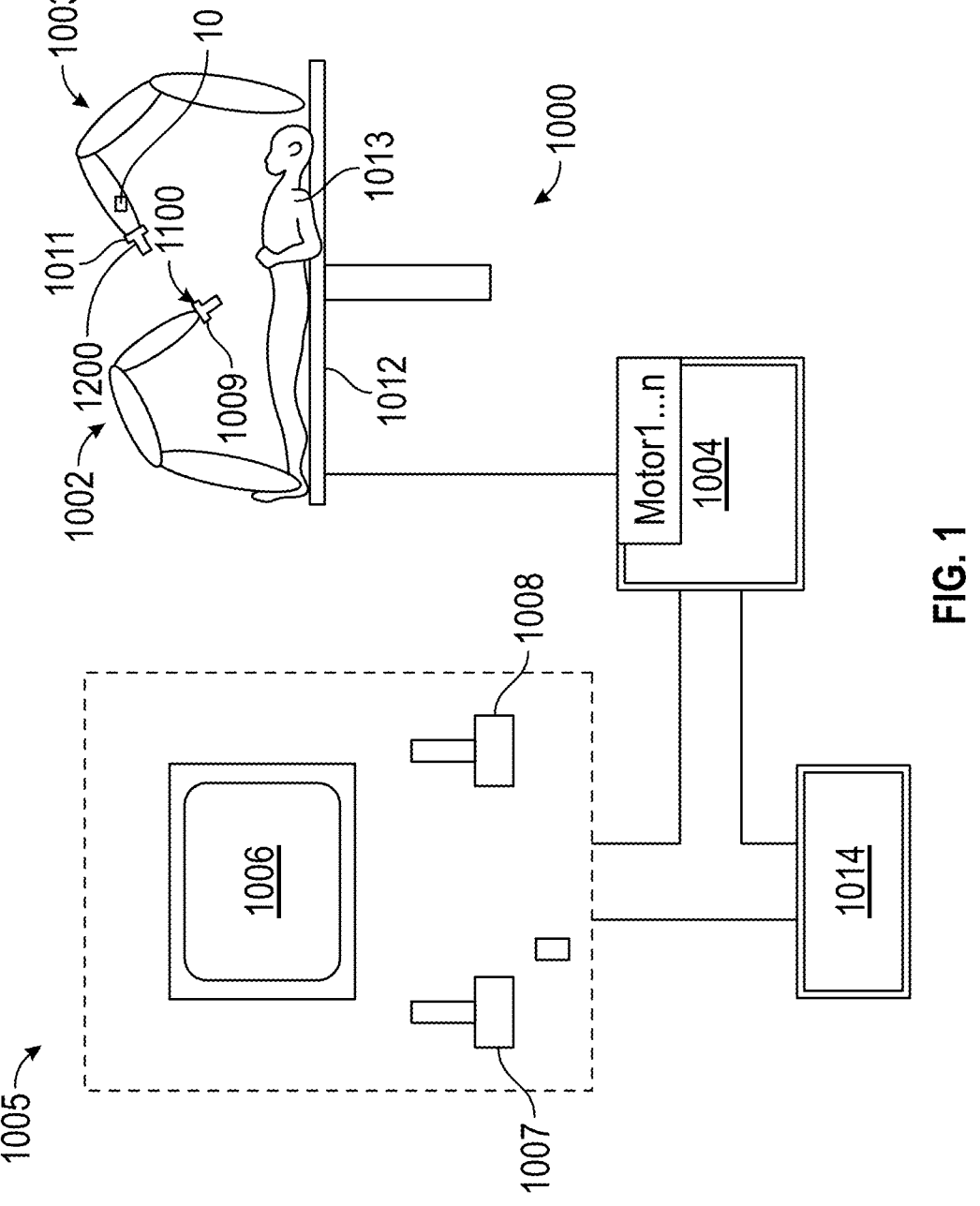
FIG. 1 is a schematic diagram of a robotic surgical system provided in accordance with aspects of the disclosure.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION

Embodiments of the disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

As used herein, the term "segmentation" includes the process of partitioning an image into multiple segments (e.g., sets of pixels). Generally, the result of segmentation is a set of segments that collectively cover the entire image.

The disclosure is applicable where images of a surgical site are captured. Endoscope systems are provided as an example, but it will be understood that such description is exemplary and does not limit the scope and applicability of the disclosure to other systems and procedures. It is contemplated that the disclosure is applicable to, for example, robotic surgical systems as well as laparoscopic, hand-operated surgery.

With reference to FIG. 1, a robotic surgical system exemplifying the aspects and features of the disclosure is shown identified by reference numeral 1000. Robotic surgical system 1000 includes a plurality of robot arms 1002, 1003; a control device 1004; an operating console 1005 coupled with control device 1004; and an endoscope system 10 coupled to the robot arm 1003. In aspects, the endoscope system 10 may be independent of the robot arm 1003. Operating console 1005 may include a display device 1006, which may be set up in particular to display three-dimensional images; and manual input devices 1007, 1008, to enable a clinician to telemanipulate robot arms 1002, 1003 in a first operating mode. Robotic surgical system 1000 may be configured for use on a patient 1013 lying on a patient table 1012 to be treated in a minimally invasive manner Robotic surgical system 1000 may further include a database 1014 coupled to control device 1004, in which pre-operative data from patient 1013 and/or anatomical atlases are stored.

Each of the robot arms 1002, 1003 may include a plurality of segments, which are connected through joints, and an attaching device 1009, 1011, to which may be attached, for example, an end effector assembly 1100, 1200, respectively. End effector assembly 1200 may be any suitable end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Manual input devices 1007, 1008 of robotic surgical system 1000 may further include a motion activation control, a motion-sensing assembly including a motor, rotation and/or articulation lockout features, excessive torque limiting features, and/or a rotation control, similarly as detailed above, to provide the user with the ability to control manipulation of end effector assemblies 1100, 1200, by moving manual input devices 1007, 1008 relative to a reference position.

Figure 2:
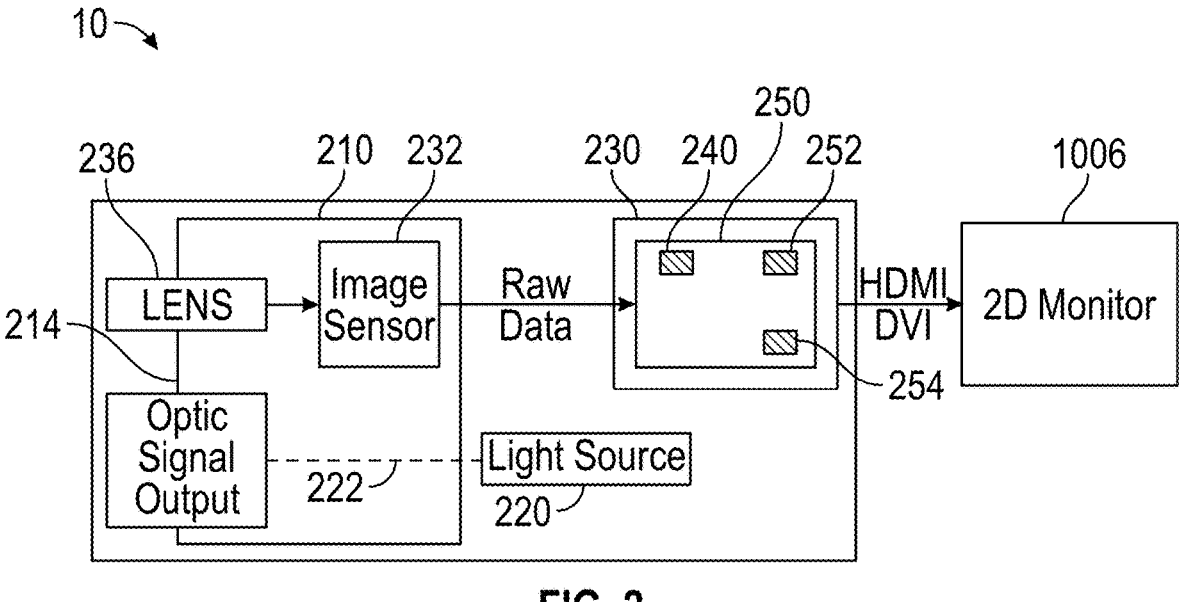
FIG. 2 is a schematic diagram of a visualization system for use in the robotic surgical system of FIG. 1.

Referring to FIG. 2, there is shown a schematic illustration of a visualization system, such as, for example, the endoscope system 10 of the robotic surgical system 1000 shown in FIG. 1. The endoscope system 10 may be coupled to one of the robot arms (e.g., robot arm 1003) or incorporated into the end effector assembly 1200. In other aspects, the endoscope system 10 may be a stand-alone system that is independently movable relative to the robot arms 1002, 1003. The endoscope system 10 generally includes an imaging device 210 (e.g., a camera), a light source 220, a video system 230, and a display 1006. The light source 220 is configured to provide light to a surgical site via a fiber guide 222 of the imaging device 210. The imaging device 210 has a distal end portion 214 including an objective lens 236 for capturing the image at the surgical site. The objective lens 236 forwards the image to an image sensor 232 of the imaging device 210. The image is then communicated from the imaging device 210 to the video system 230 for processing. The imaging device may be a stereoscopic imaging device.

The video system 230 includes an imaging device control unit 250 for controlling the endoscope system 10 and processing images. The imaging device control unit 250 includes a processor 252 connected to a computer-readable storage medium or a memory 254 which may be a volatile type memory, such as RAM, or a non-volatile type memory, such as flash media, disk media, or other types of memory. In various embodiments, the processor 252 may be another type of processor such as, without limitation, a digital signal processor, a microprocessor, an ASIC, a graphics processing unit (GPU), field-programmable gate array (FPGA), or a central processing unit (CPU). It is contemplated that the processor 252 can be separate from the imaging device control unit 250 and can communicate with the imaging device control unit 250 through communication buses of a circuit board and/or through communication cables such as serial ATA cables or other types of cables, and/or wirelessly (e.g., via Bluetooth and/or Wi-Fi).

In various embodiments, the memory 254 can be random access memory, read-only memory, magnetic disk memory, solid-state memory, optical disc memory, and/or another type of memory. In various embodiments, the memory 254 can be separate from the imaging device control unit 250 and can communicate with the processor 252 through communication buses of a circuit board and/or through communication cables such as serial ATA cables or other types of cables. The memory 254 includes computer-readable instructions that are executable by the processor 252 to operate the imaging device control unit 250. In various embodiments, the imaging device control unit 250 may include a network interface 240 to communicate with other computers or a server.

Figure 3:
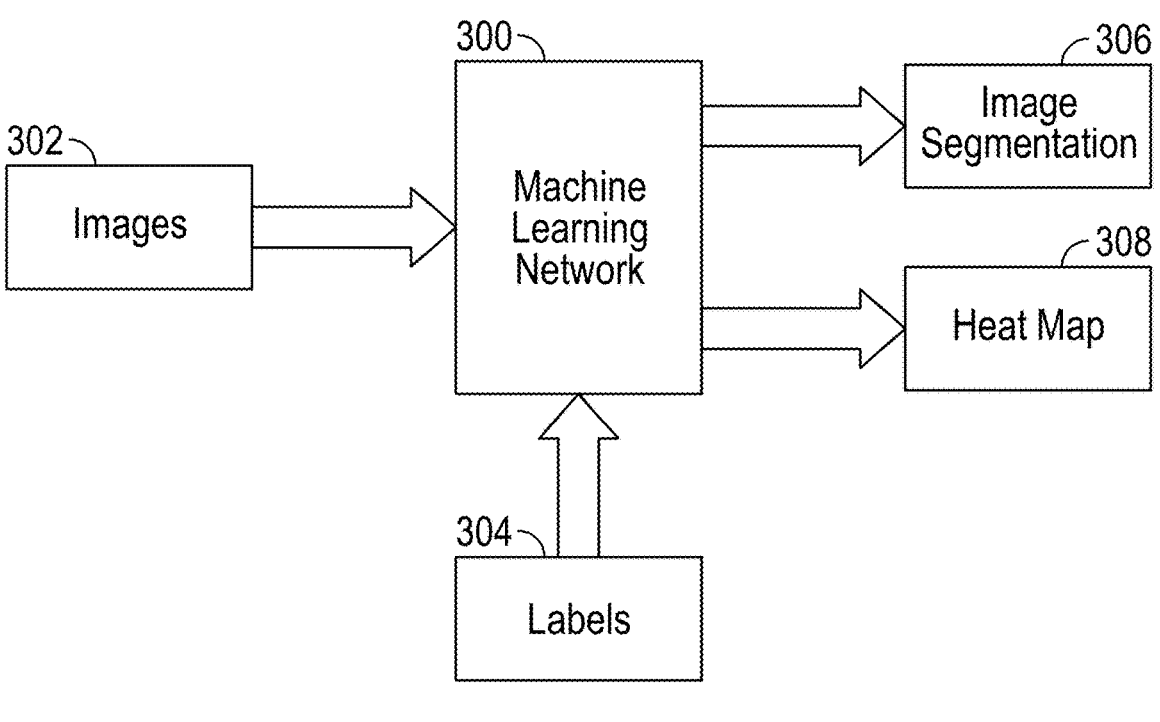
FIG. 3 is a schematic diagram illustrating a machine learning network of the visualization system of FIG. 2, in accordance with an exemplary embodiment of the disclosure.

Referring now to FIG. 3, there is shown a machine learning network 300 of the visualization system of FIG. 2. The machine learning network 300 is configured to determine a location and an estimated pose of a surgical needle (or other object) in an image. The pose may include a yaw, a pitch, and a tilt of the surgical needle (or other object). Images 302 that include a surgical needle 500 (FIG. 5) are input into a machine learning network 300. The machine learning network 300 generates a heatmap 308 and/or image segmentation 306 of the surgical needle. The images 302 may include 3D images. A 3D image may include a left image and a right image.

Figure 4:
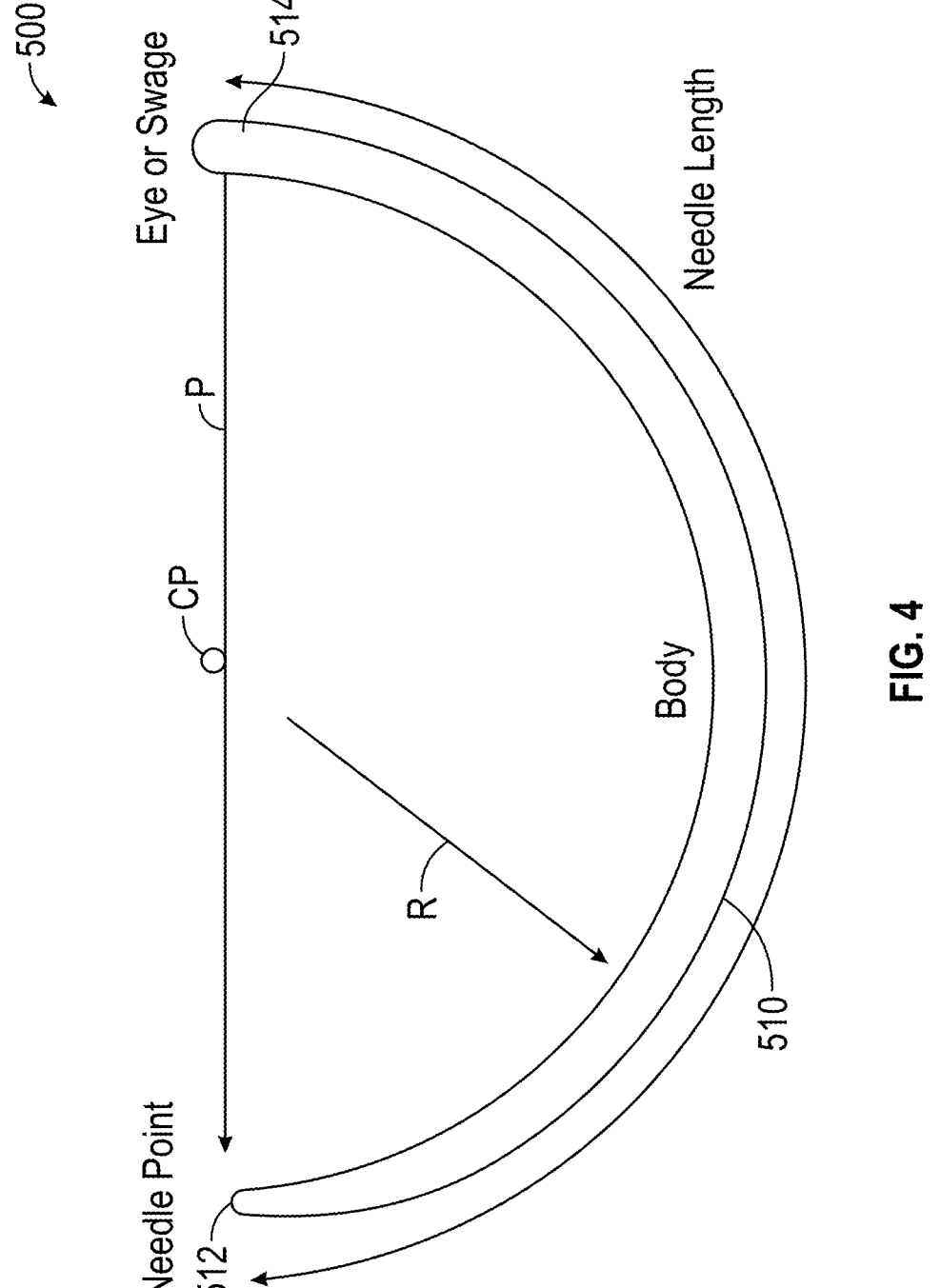
FIG. 4 is a diagram of a surgical needle in accordance with an exemplary aspect of the disclosure.

For example, the machine learning network 300 may take the left and the right image from the 3D image and segment the surgical needle in each of the left image and right image to generate a pixel-wise segmentation of the surgical needle body 510 and the surgical needle tip 502 (FIG. 4). This segmentation of the surgical needle body 510 and the surgical needle tip 502 may be used to generate a 3D model of the surgical needle by fusing the left and right segmentations using epipolar geometry and triangulation while leveraging the endoscopic device's calibration.

The machine learning network 300 may include a neural network. In machine learning, a convolutional neural network (CNN) is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are used to train neural networks. A CNN typically includes convolution layers, activation function layers, and pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

The neural network is trained based on tagging objects in training images, and wherein the training further includes augmenting the training images to include adding noise, changing colors, hiding portions of the training images, scaling of the training images, rotating the training images, and/or stretching the training images. In various embodiments, the training includes supervised, unsupervised, and/or reinforcement learning. It is contemplated that the training may be performed by a processor external to the video system 230. Training of the artificial intelligence learning network may be based on, for example, images of suture procedures performed by clinicians or robotic surgical systems, which are labeled with regard to simulation-derived pressure across a tissue-to-tissue interface, suturing adjustments, suggested remedial actions, and/or success of outcomes. The images or videos of suture procedures performed by clinicians or robotic surgical systems may be used for machine learning to improve the initial placement of the suture at the target location prior to simulation. The pressure across a tissue-to-tissue interface during the simulation of suturing configurations may be determined by the trained artificial intelligence learning network to assist with more accurately and quickly determining the most effective suturing configuration. In various embodiments, a trained artificial intelligence learning network may be able to analyze images/videos of a suturing site and provide a suturing configuration for the suture site without the need for simulations.

The terms "artificial intelligence," "learning machine," and "machine learning" may include, but are not limited to, neural networks, deep neural networks, Bayesian Regression, Naive Bayes, Monte Carlo Methods, nearest neighbors, least squares, means, and support vector regression, among other data science and artificial science techniques. Exemplary implementations of an artificial intelligence learning network can identify patterns and making predictions relating to appropriate suture placement, as described above.

Referring to FIG. 4, a surgical needle 500 configured for suturing tissue in a surgical site is shown. The surgical needle 500 includes a body 510 and a tip 502 configured for piercing tissue during the suturing process. The surgical needle 500 further includes/defines a radius or radius of curvature "R" and a center point "CP" of the radius "R". The body 510 of the surgical needle defines a flat or body plane "P".

Figure 5:
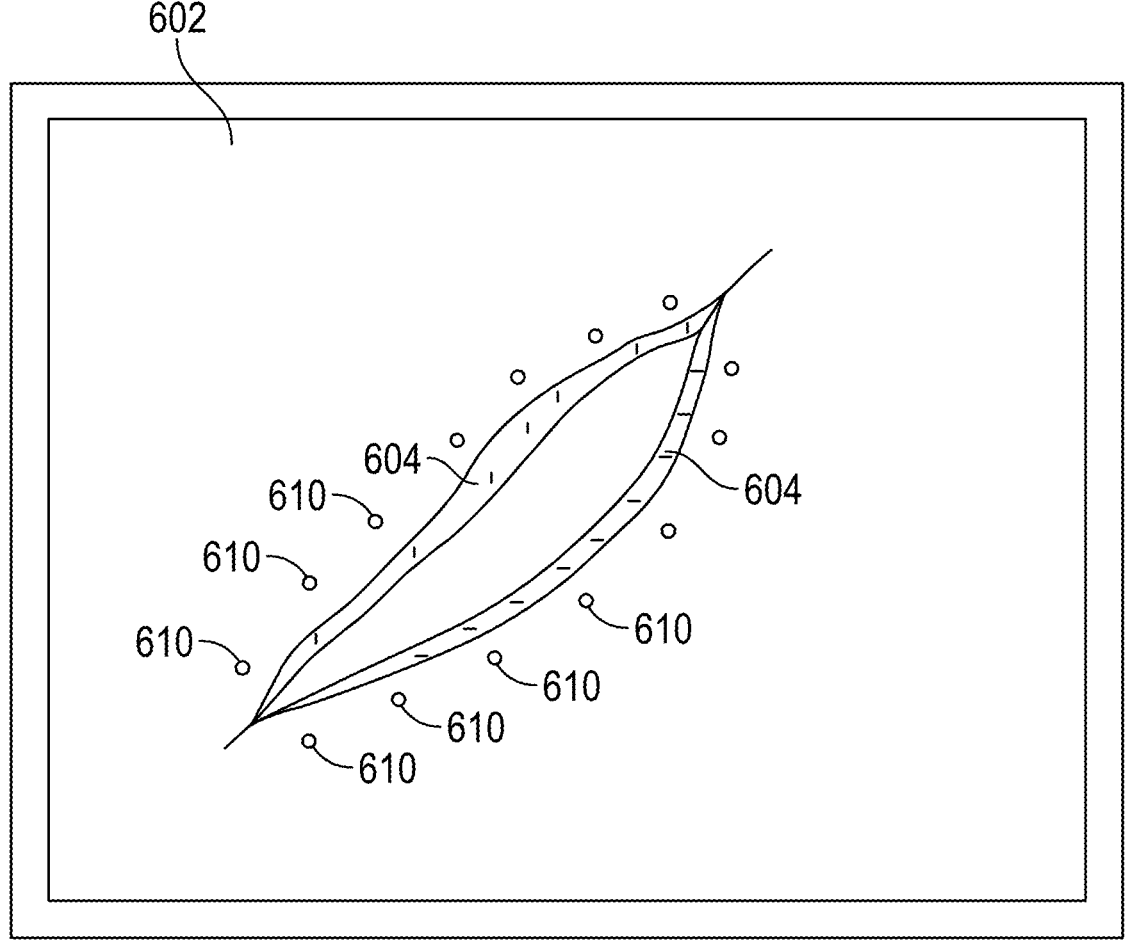
FIG. 5 is a diagram of a display showing an exemplary suture site, in accordance with aspects of the disclosure, prior to a surgical suturing procedure.
Figure 6:
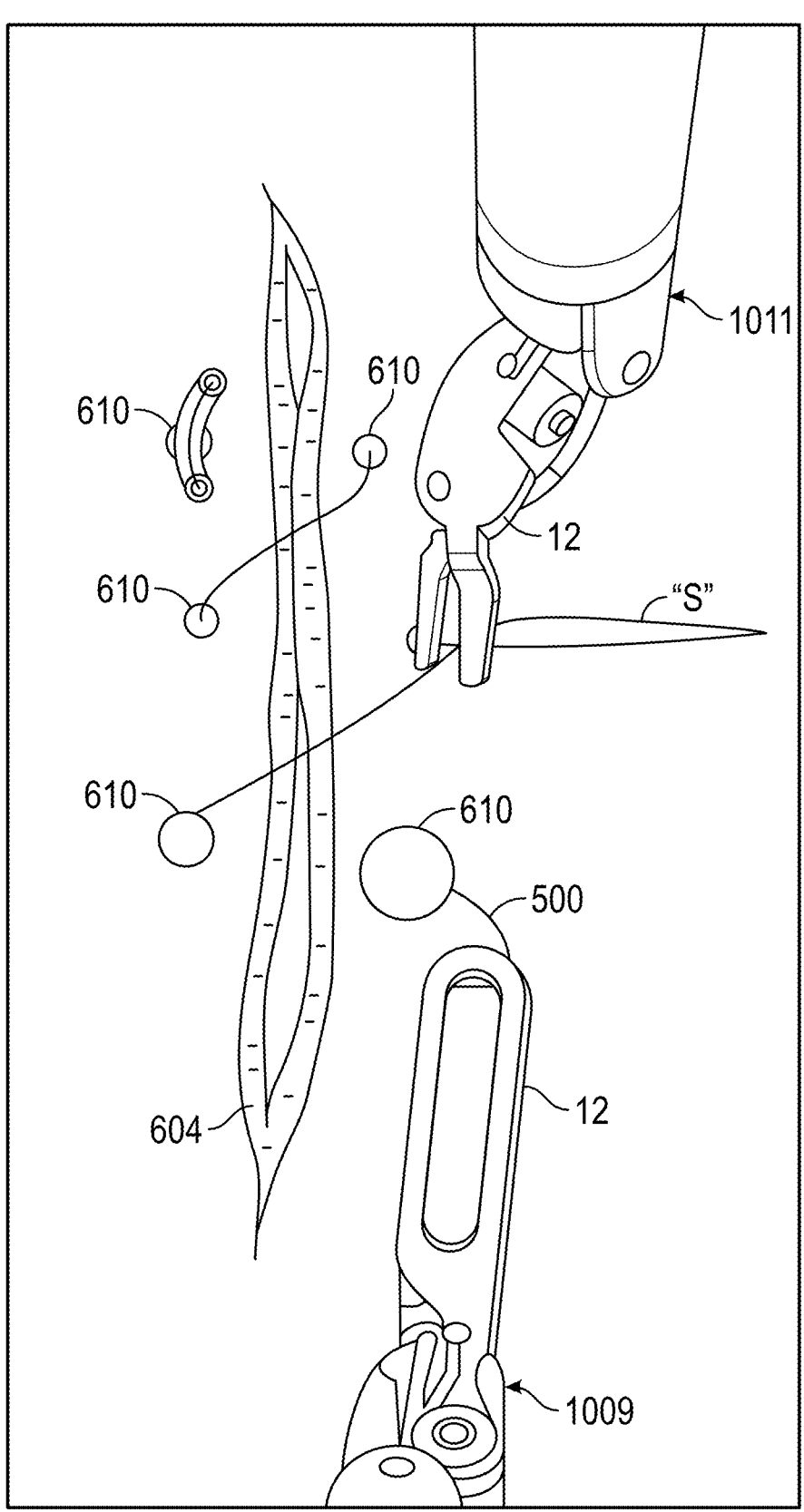
FIG. 6 is a diagram of the display showing the exemplary suture site of FIG. 5 during the surgical suturing procedure.

FIGS. 5 and 6 show a display of an image or video of an exemplary suture site 602 captured by an endoscope system 10. As mentioned above, the suture site 602 can be on a person's body or within a person's body. Clinicians generally rely on their own judgment and experience for placing sutures to re-approximate tissue. The objective is to place tissue faces 604 in approximation to one another in a way that allows as much as possible of those tissue faces 604 to be in contact and to do so with the appropriate pressure to be placed upon and maintained over the entirety of the tissue interface. Parameters for achieving that objective include: choice of the type of suture "S" and its attached surgical needle 500, placement location/pathway, frequency of suture loops, and/or the tension of the suture "S" created in the process of knot creation, among other parameters. In accordance with aspects of the disclosure, the system may provide tissue suturing guidance for assessing a suture site 602 to provide recommendations with respect to such parameters to a clinician.

As an example, the image/video of the suture site can be augmented, in real-time, to include markers 610 that indicate the suture/needle placement locations and/or pathway for re-approximating the tissue of the suture site 602. As described below, the locations of the markers 610, among other things, can be determined, in real-time, by the tissue suturing guidance system and can be dynamically updated and displayed before and during the suturing procedure. Accordingly, if a clinician deviates from the indicated locations and/or pathways, the locations of the markers 610 can dynamically change based on the actual needle/suture placements performed by the clinician. For example, the markers 610 can change color from/between green/yellow/red when the locations and/or pathways are acceptable/partially-acceptable/not-acceptable, or the markers 610 can begin to pulse, change shape, or the like for any predetermined condition.

Figure 7:
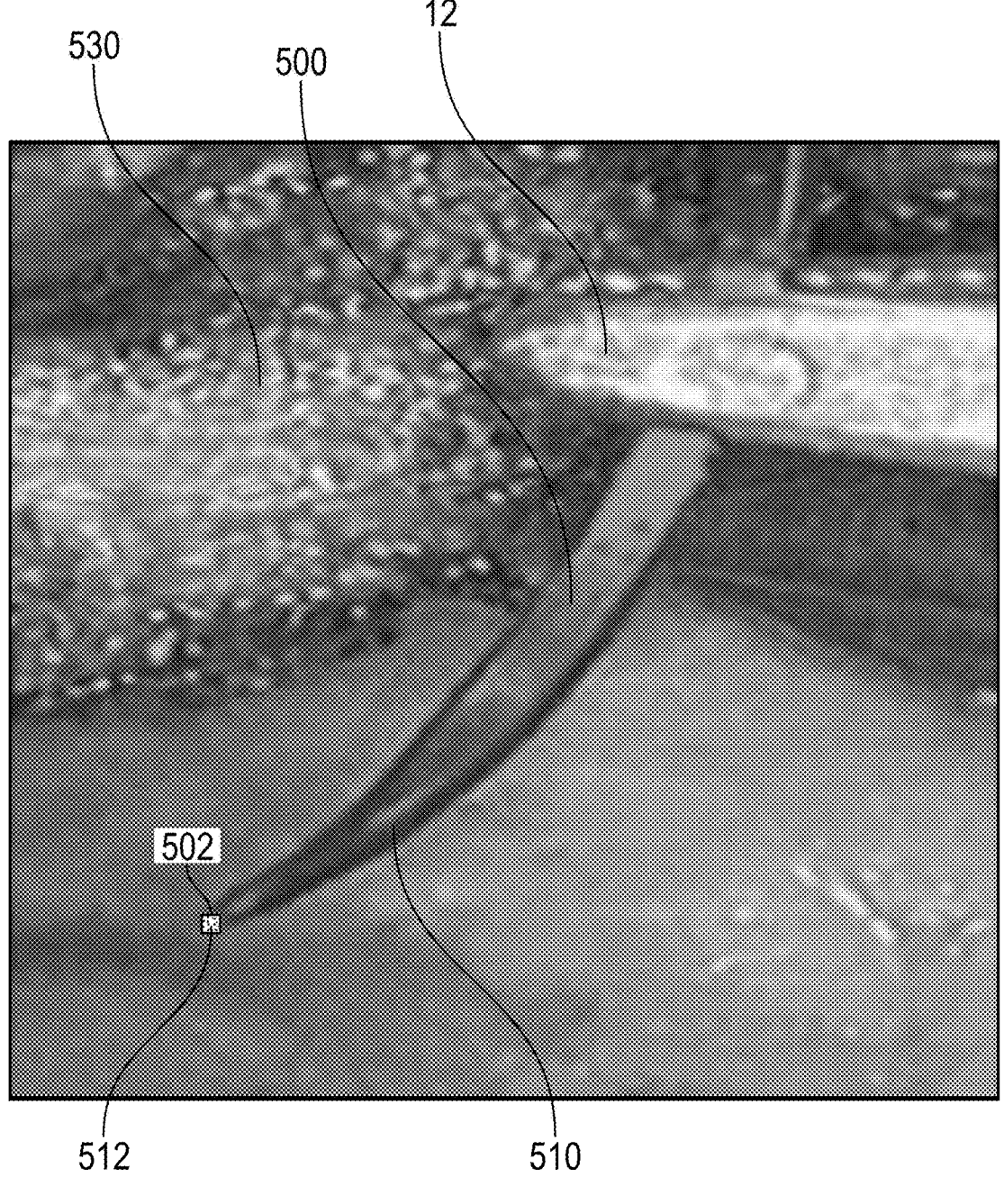
FIG. 7 is an image of a surgical needle with a prediction overlay in accordance with an exemplary aspect of the disclosure.

FIG. 7 shows an image of a surgical needle with a prediction overlay. The image includes the surgical needle 500, jaws 12 of a surgical tool, and tissue of a patient 1013. The video system 230 may augment the image by including a prediction overlay over the surgical needle 500 and/or the surgical needle tip 502. The prediction overlay may be based on a 3D model generated by the machine learning network 300. In aspects, the prediction overlay may allow a clinician to "see" the body 510 and/or the tip 502 even when it is covered by tissue.

Figure 8:
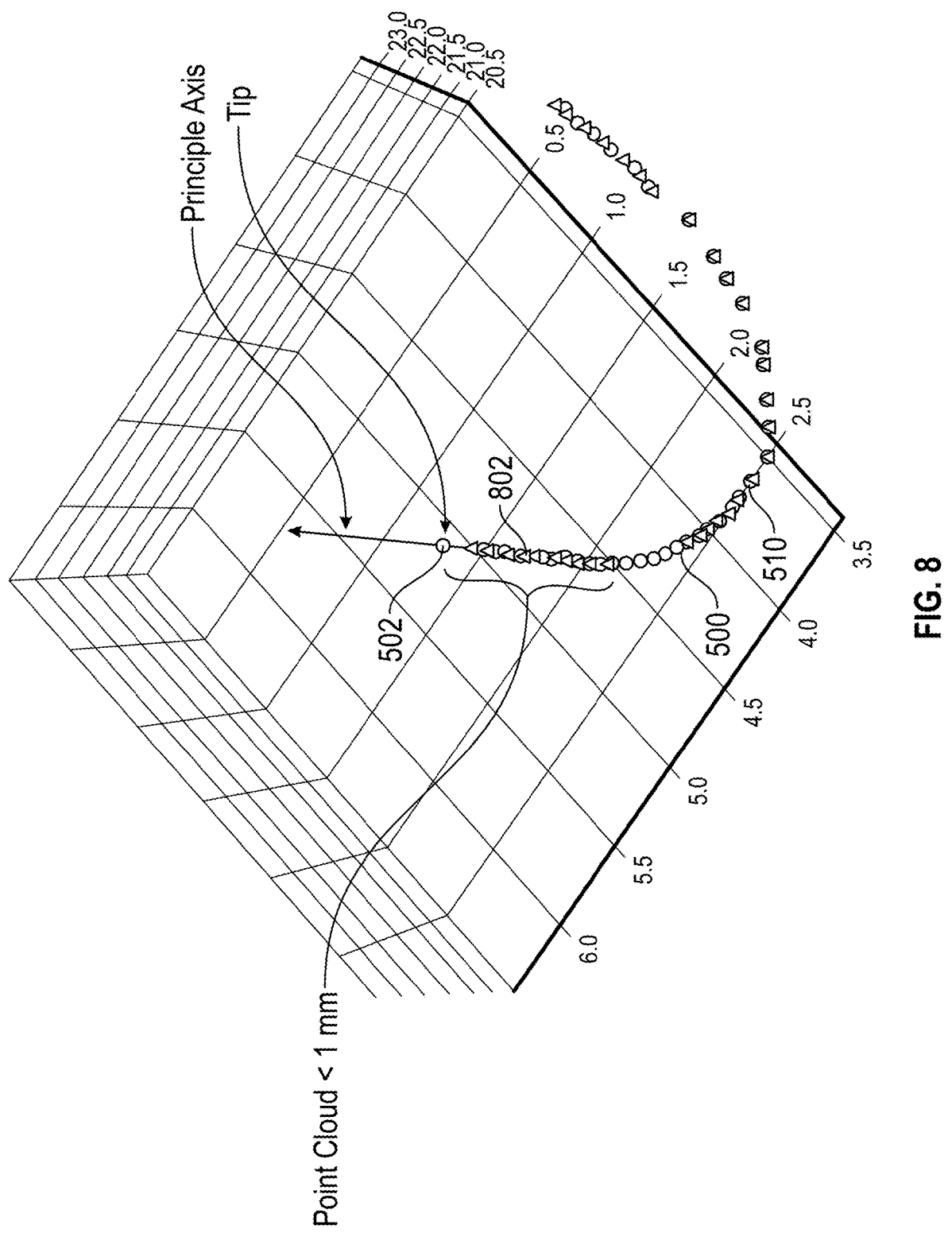
FIG. 8 is an image of a surgical needle with a prediction overlay in accordance with an exemplary aspect of the disclosure.

FIG. 8 is an image showing an estimation of a direction of the surgical needle tip 502. The system may take the 3D model generated by the machine learning network's left and right segmentation of the surgical needle and estimate a direction of the tip 502 of the surgical needle 500 based on the 3D points 802 of the body 510 of the surgical needle 500.

Figures 9A, 9B:
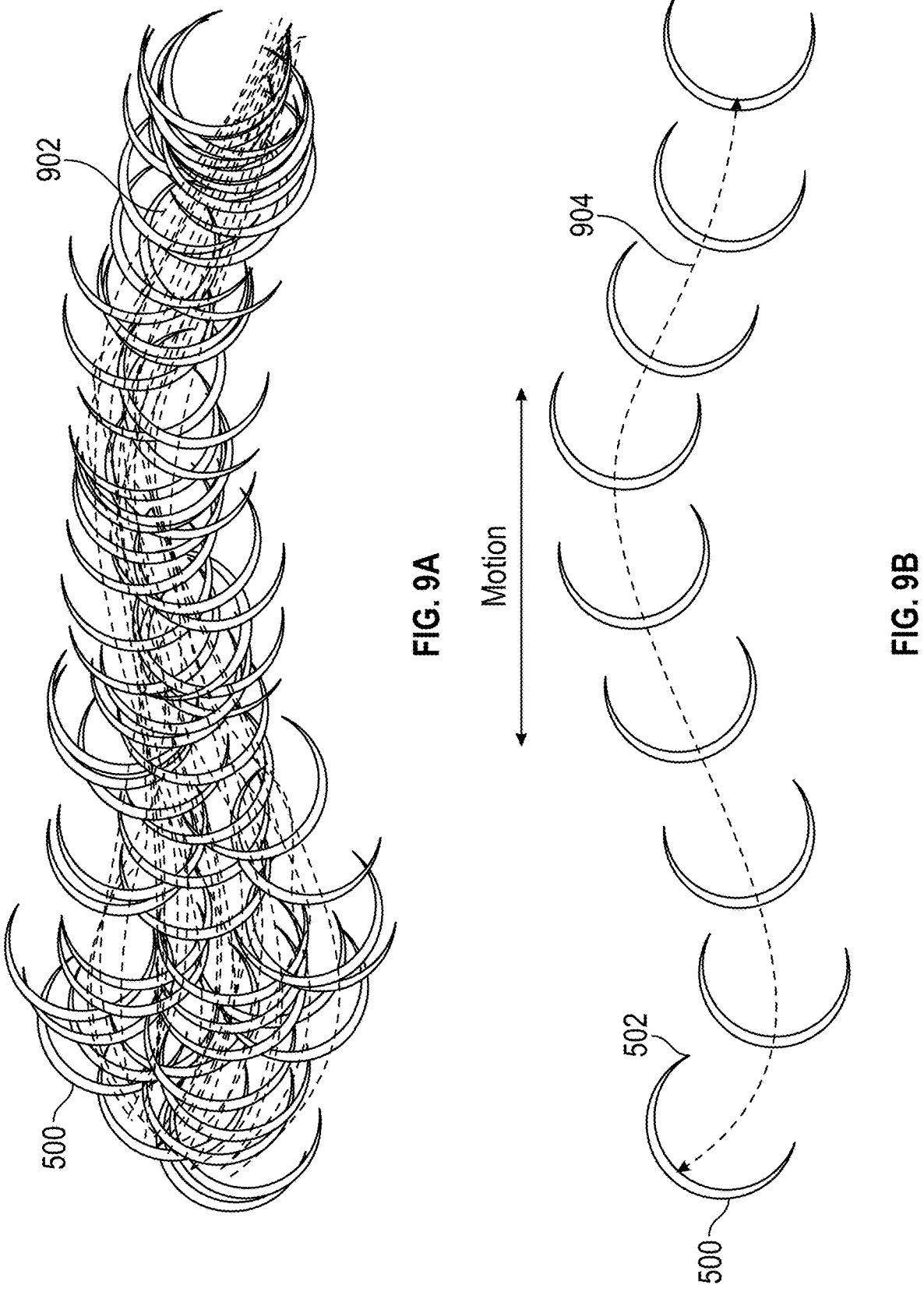
FIGS. 9A and 9B are images of position refinement of the surgical needle trajectory in accordance with an exemplary aspect of the disclosure.

FIG. 9A illustrates exemplary clinician commanded surgical needle 500 trajectories 902. For example, when the clinician commands the robotic surgical system 1000 to stitch the tissue, there may be some variation in the trajectory.

FIG. 9B illustrates position refinement of the surgical needle 500 trajectory 904 based on the estimated pose of the surgical needle 500 and/or tip 502 of the surgical needle 500.

The flow diagram of FIG. 10 described below includes various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by the video system 230, but those skilled in the art will appreciate that the video system 230 is exemplary. In various embodiments, the disclosed operations can be performed by another component, device, or system. In various embodiments, the video system 230 or other component/device performs the actions or tasks via one or more software applications executing on the processor 252. In various embodiments, at least some of the operations can be implemented by firmware, programmable logic devices, and/or hardware circuitry. Other implementations are contemplated to be within the scope of the disclosure.

Figure 10:
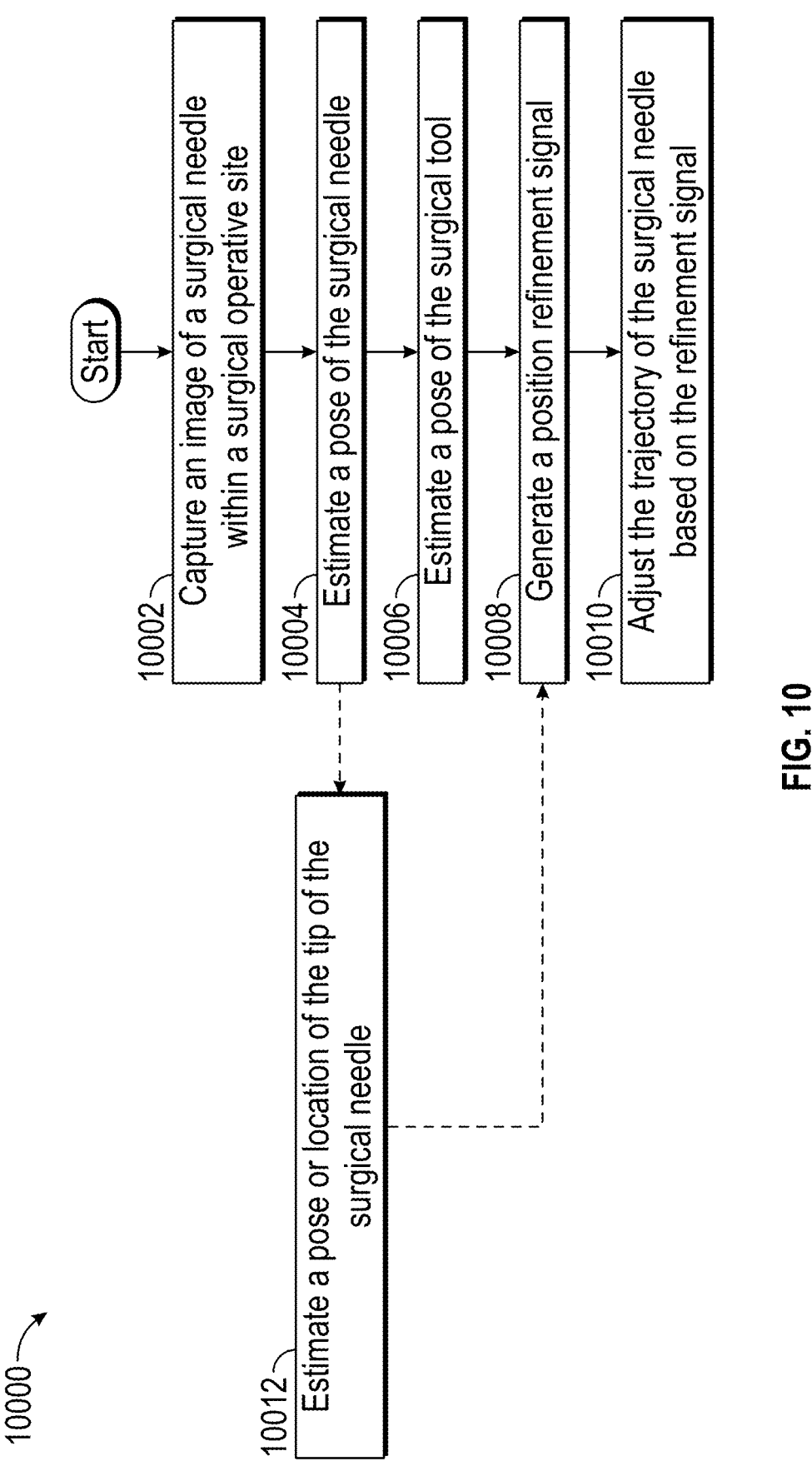
FIG. 10 is a flow diagram of an exemplary operation of generating a suture configuration for a suture site, in accordance with aspects of the disclosure.

Referring now to FIG. 10, there is shown an exemplary operation 10000 for surgical needle location detection in endoscopy images performed by the endoscope system 10. Initially, at step 10002, the video system 230 captures an image of the surgical needle 500 (FIG. 4) within the surgical operative site.

The video system 230 accesses the image, and at step 10004, the video system 230 estimates a pose of the surgical needle 500 within a field of view (FOV) of the imaging device 210. The video system 230 may use a machine learning network 300 to perform image segmentation to estimate the pose (and/or location) of the surgical needle 500 and/or the tip 502 of the surgical needle 500. The estimated pose may include a yaw, a pitch, and/or a tilt of the surgical needle 500 (or other object). It is contemplated that the surgical needle 500 may be posed anywhere between parallel to the tissue to perpendicular to the tissue in the image. In aspects, the video system 230 may estimate the location of the tissue surface based on the captured image.

For example, the video system 230 may use a visual hull algorithm to reconstruct a three dimensional shape of the surgical needle. A visual hull is a geometric entity created by shape-from-silhouette 3D reconstruction technique. This technique assumes the foreground object in an image can be separated from the background. Under this assumption, the original image can be thresholded into a foreground/background binary image, which we call a silhouette image. The foreground mask, known as a silhouette, is the 2D projection of the corresponding 3D foreground object. Along with the camera viewing parameters, the silhouette defines a back-projected generalized cone that contains the actual object. This cone is called a silhouette cone. The intersection of the two cones is called a visual hull, which is a bounding geometry of the actual 3D object. For example, a three dimensional central line of the needle may be reconstructed by triangulation of the central line points which may be based on stereo image pairs. In aspects, triangulation of central lines may be performed for each point in one line with all the points located near the epipolar line in a second line.

In aspects, the video system 230 may use a machine learning network 300 to determine whether the tip of the surgical needle is touching tissue. The video system 230 may use a machine learning network 300 to generate a heatmap based on the estimation. In aspects, the video system 230 may augment the image based on the determination of whether the tip of the surgical needle is touching tissue.

In aspects, the video system 230 may use a machine learning network 300 to estimate the pose of the surgical needle 500. Pose estimation is a process of predicting the transformation of an object from a user-defined reference pose, given an image or a 3D scan. The estimated pose or transformation of the surgical needle may be used for identification, grasping, and/or manipulation of the surgical needle.

The video system 230 accesses the image, and at step 10006, the video system 230 estimates a pose of the surgical tool (e.g., jaws 12 of FIG. 6) within a field of view (FOV) of the imaging device 210. The video system 230 may use a machine learning network 300 to perform image segmentation to estimate the pose of the surgical tool.

The video system 230 accesses the image, and at step 10012, the video system 230 estimates a pose, location, and/or direction of the tip 502 of the surgical needle 500 within a field of view (FOV) of the imaging device 210. The video system 230 may use a machine learning network 300 to perform image segmentation to estimate the pose and/or location of the tip 502.

At step 10008, the video system 230 generates a position refinement signal. The position refinement signal may be based on the estimated pose of the surgical needle 500, the estimated pose of the surgical tool, and or the estimated pose of the tip 502 of the surgical needle. For example, the video system 230 may base the position refinement signal on only the estimated pose of the surgical tool and the tip 502. The position refinement signal may be based on the perceived location of the tissue and/or other robotic/kinematic considerations.

At step 10010, the robotic surgical system 1000 adjusts the trajectory of the surgical needle based on the position refinement signal (see FIG. 9B). For example, the video system 230 may take the yaw, pitch, and tilt of the surgical needle 500, and combine it with the yaw, pitch, and tilt of the jaws 12 (FIG. 6) to feed the motion and path of a suture. In various embodiments, the video system 230 may determine tracking information for the tip of the surgical needle based on the estimated pose of the tip. In various embodiments, the video system 230 may display the tracking information of the surgical needle on the display 1006. In various embodiments, the video system 230 may use the tracking information to track the trajectory or path of the surgical needle for optimizing surgical steps. This has the benefit of suturing the desired stitch location and placement.

In some embodiments, the video system 230 may further receive input from a clinician or robotic surgical system of a desired placement of the surgical needle 500 and/or the suture "S" in the suture site. In practice, the clinician or the robotic surgical system manipulates jaws 12 of a surgical tool to change a location and pose of the surgical needle 500, and to draw the suture "S" through the tissue. Based on the desired placement, the video system 230 adjusts the suturing configuration by simulating the desired placement based on the geometric and biomechanical tissue representations of the suture site. The suture configuration is adjusted to increase the effectiveness of the suture configuration in view of the desired placement. The video system 230 causes the display 1006 to display, in real-time, the suture configuration by overlaying the suture configuration over the image of the suture site.

In some embodiments, the video system 230 of the robotic surgical system 1000 is further configured to update the suture configuration during progression of a suture procedure by either a clinician or robotic surgical system. In updating the suture configuration during progression of the suture procedure, the video system 230 uses the already placed sutures "S" in the geometric and biomechanical tissue representations and determines a suture configuration for the remainder of the suture site. The video system 230 causes the display 1006 to display, in real-time, the updated suture configuration by overlaying the updated suture configuration over the image of the suture site.

Additionally, in embodiments, the robotic surgical system 1000 may be configured to provide assessment and feedback during the progression of the suture procedure and display the assessment and feedback of the progression of the suture procedure on display 1006. Feedback of the progression of the suture procedure may include, for example, real-time simulation-derived estimates of the pressure across a tissue-to-tissue interface and a suture-tissue contact to determine if there is inadequate or excessive pressure on the tissue interface. In the event, the assessment and feedback provided by the robotic surgical system 1000 estimates that there is inadequate or excessive pressure on the tissue interface, the robotic surgical system 1000 may provide an alert and/or remedial actions to adjust pressure across a tissue-to-tissue interface.

In accordance with an embodiment of the disclosure, the robotic surgical system 1000 and/or the video system 230 are configured and capable of: (1) using image processing, in real-time, to assess the location and pose of the surgical needle 500 relative to the jaws 12; and (2) establishing the combined surgical tool-needle kinematics. Once the surgical tool-needle kinematics have been established the robotic surgical system 1000 and/or the video system 230 is/are able to simulate desired tool/needle trajectories similar to the ways these trajectories. In this manner, one or more of sub-tasks 2-8 (detailed above) can now be performed automatically or manually per the clinician's choice. Specifically, these sub-tasks include one or more of: (2) grasping a needle perpendicularly to a pair of jaws; (3) envisioning of the needle trajectory; (4) approximating the abating tissue to the envisioned needle exit site; (5) inserting a tip of a needle (e.g., a curved needle) in the desired location; (6) rotating the surgical needle 500 in a trajectory that follows the needle curvature "C"; (7) grasping the protruding surgical needle 500 or tip of the surgical needle 500; and (8) pulling the surgical needle 500 out in a path that follows the needle curvature "C".

It is further contemplated, in accordance with the disclosure, that the robotic surgical system 1000 and/or the video system 230 is/are capable of: monitoring and identifying an appropriate needle penetration point (marker 610), and virtually mark it by "pointing" a tip 502 of the surgical needle 500 at that penetration point; using image processing to identify the location, orientation, and pose of the surgical needle 500 in the jaws 12; generating a path (a circle or arc in the case of a curved needle) that simulates in 3D the needle trajectory; enabling the clinician to bring the abating tissue to the expected needle exit point; enabling the clinician to command the system to execute the suturing task; and enabling the clinician to grasp the protruding surgical needle 500 and command the robotic surgical system 1000 and/or the video system 230.

As discussed above, the disclosure relates to using vision to identify the orientation of the surgical needle 500 with respect to the jaws 12, and then updating the kinematic controller to allow the user, and to allow the automatic motion planning, to place the tip 502 of the surgical needle 500 and follow the curvature path defined by the curve of the surgical needle 500.

In a further embodiment, in accordance with the disclosure, the robotic surgical system 1000 and/or the video system 230 is/are capable of assessing properties of the underlying tissue which is the target for suturing, e.g., suture site 602 and/or tissue faces 604. The tissue properties may include and are not limited to tissue integrity (such as identifying the extent of thermal damage from cautery); tissue density, and stiffness (to ensure that selected surgical needle 500 is appropriately gauged to be able to penetrate the tissue without breaking); and presence of tissue scarring (wherein barbed sutures "S" may be used to help penetrate the tissue). The robotic surgical system 1000 and/or the video system 230 may be capable of identifying a distance between a proposed needle penetration point (e.g., marker 610) and an edge of the tissue (e.g., tissue face 604) and/or a location of where the tissue separates or an incision begins/ends.

As briefly mentioned above, the robotic surgical system 1000 and/or the video system 230 is/are capable of identifying properties of the surgical needle 500 and/or the material of the suture "S", for example, and not limited to, a thickness or gauge of the surgical needle 500, a radius of curvature of the surgical needle 500, a diameter of the suture "S", and/or a surface feature of the suture "S" (e.g., barbed or non-barbed/smooth).

The robotic surgical system 1000 and/or the video system 230 may be capable of issuing warnings to a surgeon of clinician if/when the combination of the proposed needle penetration point (e.g., marker 610) and the information set forth above (e.g., properties about the tissue, surgical needle 500 and/or suture "S") may lead to undesired impact on the tissue and the like.

Further, the robotic surgical system 1000 and/or the video system 230 may be capable of providing guidance to the direction of movement and/or orientation of the surgical needle 500, prior to or during a surgical suturing procedure whereby the robotic surgical system 1000 and/or the video system 230 provides information to the robotic surgical system to adjust the robotic surgical arms and components thereof so as to make adjustments to the surgical suturing procedure to ensure that the surgical suturing procedure may be completed within the kinematic joint limits of the robotic surgical system.

However, in accordance with a further aspect of the disclosure, the robotic surgical system 1000 and/or the video system 230 is/are capable of, may be modified to or configured to include a vision guidance system for identifying and tracking an electronic radiation source (not shown) that is used in intra-operative radiation therapy procedures and applied to potential cancer sites after a tumor or the like is removed. For example, the radiation source may be grasped by the jaws 12 of a surgical tool. The vision guidance system could identify the orientation of the radiation source relative to the jaws 12 and then treat the "jaw-instrument" assembly as a new end-effector. The vision guidance system could then scan the radiation source in a predefined path over the target tissue to cover the entire area with a uniform and known dose of radiation. The robotic surgical system may then alter kinematic equations for movement of robotic surgical arms to adjust for the "jaw-instrument" assembly. While this may be achieved mechanically by using a jig or the like to align the surgical tool in a predefined configuration with the jaws 12, by using the vision guidance system to determine the relative position between the radiation source and the jaws 12, a more flexible approach is possible and any grasped orientation of the radiation source by the jaws 12 may be used.

It is further envisioned and contemplated in accordance with the disclosure that a vision guidance system may be used to identify the surgical tool and an orientation of an item grasped by the jaws 12 of the surgical tool relative to the jaws 12 and/or the surgical tool; monitor the grasped orientation during a surgical task or procedure and actively adjust the kinematics and dynamics of the movement of the surgical tool and/or the surgical robotic arms and the like; track the target tissue and adjust the motion of the surgical tool and/or the surgical robotic arms accordingly; measure a deflection of the surgical tool and adjust the kinematics/ dynamics of the end-effector accordingly (e.g., for non-rigid surgical tool like a bare laser fiber and the like); identify a three-dimensional ("3D") position of the surgical tool relative to the jaws 12; and/or provide information to the robotic surgical system such that the robotic surgical system may adjust the kinematics and dynamics of the robotic surgical arm to control the jaw/surgical tool assembly as part of an end-effector thereof.

It is also contemplated, and in accordance with the disclosure, that the surgical tool may be a tactile probe, whereby the robotic surgical system may then combine any tactile feedback from the surgical tool into the adjusted kinematics for the surgical robotic arms.

In accordance with the disclosure, it is further contemplated that the robotic surgical system 1000 and/or the video system 230 may be tuned or configured to recognize and track the suture "S" as well. Specifically, the robotic surgical system 1000 and/or the video system 230 may recognize and track the orientation and length on the suture "S". In an embodiment, it is contemplated that the suture "S" may be provided with metrical markings along an entire length thereof, and the robotic surgical system 1000 and/or the video system 230 may be configured to recognize and track these metrical markings of the suture "S" to determine and calculate of a length of the suture "S" is increasing or stretching during the surgical procedure, over time. In this manner, the robotic surgical system 1000 and/or the video system 230 may provide feedback to the robotic surgical system whereby the robotic surgical system and/or controller/video system 230 thereof may make real-time active adjustments to the surgical robotic arm and/or the surgical tool to accommodate for any changes in the length of the suture "S."

In aspects, the robotic surgical system 1000 may use the refinement signal to adjust the depth of stitch. For example, a desired stitch may be where the center point "C" (FIG. 4) of the radius "R" of the surgical needle 500 is at the tissue surface during suturing. The robotic surgical system 1000 may determine the center point "C" based on the estimated pose of the surgical needle 500. Based on the refinement signal and the determined center point "C", the robotic surgical system 1000 may correct for a stitch that would otherwise be too shallow or too deep. Other desired depths of stitch are contemplated by this disclosure, e.g, for a shallow stich, the center point "C" of the radius "R" may be guided by the robotic surgical system 1000 along a trajectory located above the tissue surface, and for a deep stich, the center point "C" of the radius "R" may be guided by the robotic surgical system 1000 along a trajectory located below the tissue surface.

While it is desired for the surgical needle 500 to be held in the jaws 12 of the robotic surgical system 1000, such that the plane "P" of the surgical needle 500 is held substantially perpendicular to a longitudinal axis of the jaws 12, it is contemplated, in certain aspects, that the surgical needle 500 may be grasped by the jaws 12 such that the plane "P" of surgical needle 500 is non-perpendicular relative to the longitudinal axis of the jaws 12, and that the vision system may be used to make adjustments to the operation (e.g., the kinematics) of the robotic surgical system 1000, as needed or desired.

Surgical needles 500 may be flexible and can bend, changing the arc of the surgical needle 500. The robotic surgical system 1000 can also compensate for cases where the surgical needle 500 is bent by estimating the pose of the bent surgical needle 500 and adjusting the trajectory based on the new arc/shape of the surgical needle.

In aspects, the video system 230 may display the surgical needle 500 of the captured image on the display 1006 (FIG. 2). In various embodiments, the display may include a tablet, a mobile device, a sub-window displayed on the display 1006, and/or an AR/VR device. In aspects, the video system 230 may be configured to augment (e.g., highlight) the image of the surgical needle 500 and/or the tip 502 of the surgical needle 500 shown on the display 1006 in a more visible color relative to the rest of the displayed image. The augmentation may include a visual warning, including a changing of the color of the displayed surgical needle and/or the tip of the surgical needle on the display 1006. The augmented image may be displayed on a 2D and/or a 3D display device.

The phrases "in an embodiment," "in embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms, or codes may be converted or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Python, MATLAB, Simulink, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms, or codes may be contained on one or more machine-readable media or memory. The term "memory" may include a mechanism that provides (for example, stores and/or transmits) information in a form readable by a machine such as a processor, computer, or a digital processing device. For example, a memory may include read-only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the disclosure. Various alternatives and modifications can be devised by those skilled in the art without departing from the disclosure. Accordingly, the disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for tissue suturing guidance in a surgical site, the system comprising:
    an imaging device configured to capture stereoscopic image data of a surgical needle within the surgical site; and
    an imaging device control unit configured to control the imaging device, the imaging device control unit including:
    a processor; and
    a memory storing instructions which, when executed by the processor, cause the system to:
        capture stereoscopic image data comprising an image of a surgical needle and a surgical tool within the surgical site via the imaging device;
        estimate a pose of the surgical needle based on the captured stereoscopic image data;
        generate an augmented image based on the estimated pose of the surgical needle; and
        display on a display, the augmented image of the surgical needle.

2. The system of claim 1, wherein the instructions, when executed by the processor, further cause the system to:
    estimate a pose of the surgical tool based on the captured stereoscopic image data; and
    generate a position refinement signal based on the estimated pose of the surgical needle and the estimated pose of the surgical tool.

3. The system of claim 2, wherein the instructions, when executed by the processor, further cause the system to:
    receive a first control signal for the surgical tool;

generate a second control signal based on the position refinement signal and the first control signal; and adjust a trajectory of the surgical needle based on the second control signal.

4. The system of claim 1, wherein estimating the pose of the surgical needle, is based on a machine learning network.

5. The system of claim 3, wherein the instructions, when executed by the processor, cause the system to:

estimate a location of a tip of the surgical needle based on the captured stereoscopic image data.

6. The system of claim 5, wherein the instructions, when executed by the processor, further cause the system to:

generate a third control signal for adjusting a trajectory of the surgical needle based on the estimated pose of the tip of the surgical needle.

7. The system of claim 5, wherein the instructions, when executed by the processor, further cause the system to:

determine whether the tip of the surgical needle is touching tissue; and further augment the augmented image based on the surgical needle touching the tissue.

8. The system of claim 7, wherein the instructions, when executed, further cause the system to:

generate a third control signal for controlling a robotic surgical system based on the determined touch of the tissue by the tip of the surgical needle.

9. The system of claim 5, wherein the augmented image includes at least one of highlighting the surgical needle or highlighting the tip of the surgical needle.

10. The system of claim 1, wherein the stereoscopic image data comprises a left image and a right image of the surgical needle and the surgical tool.

11. A system for tissue suturing guidance in a surgical site, the system comprising:

an imaging device configured to capture stereoscopic image data of a surgical needle and a surgical tool within the surgical site, the stereoscopic image data comprising a left image and a right image; and an imaging device control unit configured to control the imaging device, the imaging device control unit including:

a processor; and a memory storing instructions which, when executed by the processor, cause the system to:

capture, via the imaging device, the stereoscopic image data of the surgical needle and the surgical tool within the surgical site;

process the left image and the right image to generate segmentations identifying a body portion and a tip portion of the surgical needle in each of the left image and the right image;

generate, based on the segmentations and calibration data of the imaging device, a three-dimensional model of the surgical needle by fusing the left and right segmentations using triangulation;

estimate a pose of the surgical needle based on the three-dimensional model;

generate an augmented image based on the estimated pose of the surgical needle, the augmented image including a prediction overlay representing at least a portion of the surgical needle derived from the three-dimensional model; and display on a display, the augmented image of the surgical needle.

12. The system of claim 11, wherein generating the three-dimensional model of the surgical needle includes reconstructing a three-dimensional central line of the surgical needle by triangulating central line points based on stereo image pairs, including, for each point in a central line in one of the left image or the right image, triangulating with points located near an epipolar line in the other of the left image or the right image.

13. The system of claim 11, wherein estimating the pose of the surgical needle based on the three-dimensional model includes determining at least one of a yaw, a pitch, or a tilt of a central line of the surgical needle represented in the three-dimensional model.

14. The system of claim 11, wherein processing of the left image and the right image to generate segmentations is performed by a machine learning network comprising a deep neural network configured to perform pixel-wise segmentation of the body portion and the tip portion of the surgical needle in the left image and the right image.

15. The system of claim 12, wherein reconstructing the three-dimensional central line of the surgical needle includes fitting a curve to triangulated central line points to represent the central line of the surgical needle in three-dimensional space.

16. The system of claim 11, wherein the prediction overlay includes a graphical representation of a current pose of the surgical needle and a predicted trajectory of the surgical needle through tissue derived from the three-dimensional model.

17. The system of claim 14, wherein the memory further stores instructions which, when executed by the processor, cause the system to:

compute, from outputs of the machine learning network, a heatmap indicating a likelihood that the tip portion of the surgical needle is contacting tissue; and modify the prediction overlay in the augmented image in response to the likelihood that the tip portion of the surgical needle is contacting tissue exceeding a threshold.

18. The system of claim 11, wherein the memory further stores instructions which, when executed by the processor, cause the system to generate a control signal for a robotic surgical system based on at least one of the estimated pose of the surgical needle or the predicted trajectory of the surgical needle.

19. The system of claim 11, wherein the display comprises at least one of a three-dimensional display device or a head-mounted display configured to present the augmented image with depth perception corresponding to the stereoscopic image data.

20. The system of claim 11, wherein the memory further stores instructions which, when executed by the processor, cause the system to compute a confidence measure associated with the three-dimensional model of the surgical needle, and to selectively generate the prediction overlay in the augmented image in response to the confidence measure satisfying a predetermined criterion.

* * * * *